United States Patent [19]

Spry

[11] Patent Number: 4,533,497
[45] Date of Patent: Aug. 6, 1985

[54] N-ETHYLIDENE AZETIDINONES

[75] Inventor: Douglas O. Spry, Mooresville, Ind.

[73] Assignee: Eli Lilly and Company, Indianapolis, Ind.

[21] Appl. No.: 453,563

[22] Filed: Dec. 27, 1982

[51] Int. Cl.$^3$ ............... C07D 205/08; C07D 401/06; C07D 403/12; C07D 403/06
[52] U.S. Cl. ............... 260/239 A; 260/245.4; 260/330.3; 260/330.9; 544/60; 544/111; 544/359; 546/208
[58] Field of Search ............ 260/245.4, 239 A, 330.3, 260/330.9; 544/60, 111; 546/208

[56] References Cited

U.S. PATENT DOCUMENTS

| | | | |
|---|---|---|---|
| 4,065,621 | 12/1977 | Spitzer | 544/30 |
| 4,079,181 | 3/1978 | Tsuji et al. | 544/133 |
| 4,260,743 | 4/1981 | Bose | 260/239 A |
| 4,264,597 | 4/1981 | Hashimoto | 260/239 A |
| 4,342,685 | 8/1982 | Nagata | 260/239 A |

OTHER PUBLICATIONS

Plaskie, J. Antibiotics, XXXI, 783, (1978).
Robertiello et al., Annali di Chimica 67, p. 223, (1977).
Montovani et al., Gazzetta Chim Italianer 107, p. 207, (1977).
Spry et al., Chem. Abs. 100, 22463, (1983).
Tsuji et al., Chem. Abs. 97, 1273895, (1981).
Allan et al., J. C. S. Perkins I., 1973, p. 1182.
Eglington, J. C. S. Chem. Comm., 1977, p. 720.
Mantovani et al., Chem. Abs. 88, 37680q, (1977).
Robertiello et al., Chem. Abs. 88, 189446f, (1977).
Fujisawa, Chem. Abs. 93, 8196, (1979).
Plaskie, Chem. Abs. 89, 211022j, (1978).

*Primary Examiner*—Mark L. Berch
*Attorney, Agent, or Firm*—Paul C. Steinhardt; Arthur R. Whale

[57] ABSTRACT

N-ethylidene azetidinones are new antibiotic compounds. They are produced from the reaction of a Grignard reagent with a cephalosporin substituted at the 3 position with a chloro, oxy, amino or sulfide moieties.

6 Claims, No Drawings

N-ETHYLIDENE AZETIDINONES

SUMMARY OF THE INVENTION

This invention is directed to N-ethylidene azetidinone antibiotic compounds of the general formula

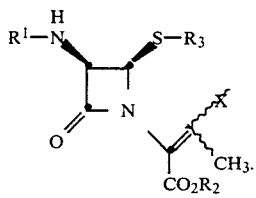

These N-ethylidene azetidinones are produced by the reaction of Grignard reagents and substrate cephalosporins which are substituted at the 3 position with chloro, oxy, amino or sulfide moieties.

DETAILED DESCRIPTION

The compounds of this invention are N-ethylidene azetidinones of the formula (1)

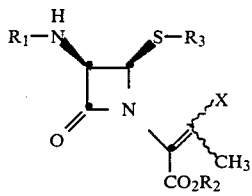    1 wherein
$R_1$ is hydrogen or an acyl group of the formula

  ;

wherein R′ is $C_1$ to $C_6$ alkyl, $C_1$ to $C_3$ cyanoalkyl, methylphenyl, hydroxyphenyl, protected hydroxyphenyl, aminophenyl, protected aminophenyl or methoxyphenyl; or
R′ is a group of the formula

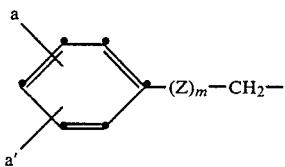

wherein a and a′ are independently hydrogen, $C_1$ to $C_4$ alkyl, $C_1$ to $C_4$ alkoxy, halogen, amino, protected amino, hydroxy, protected hydroxy, carboxy or protected carboxy,
Z is O or S, and
m is 0 or 1; or
R′ is a group of the formula

wherein P is thienyl, phenyl or a substituted phenyl group of the formula

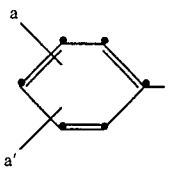

wherein a and a′ are as defined above, Q is hydroxy, protected hydroxy, amino, protected amino, carboxy or protected carboxy; or
R′ is a group of the formula

R″—CH$_2$— wherein R″ is thienyl, furyl, 2-oxazolyl, 2-thiazolyl or 1-tetrazolyl;
$R_2$ is hydrogen, methyl, benzyl, 4-methoxybenzyl, diphenylmethyl or t-butyl;
$R_3$ is $C_1$ to $C_4$ alkyl or phenyl;
X is $C_1$ to $C_4$ alkyl, phenyl, chloro, bromo, hydroxy, protected hydroxy, $C_1$ to $C_4$ alkoxy, $C_1$ to $C_4$ alkyl sulfide, a group of the formula

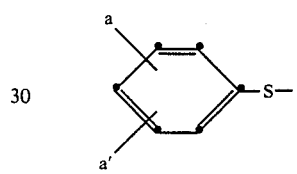

wherein a and a′ are as described above, or a group of the formula

wherein $R_5$ and $R_6$ when taken separately are independently $C_1$ to $C_4$ alkyl, benzyl or phenylethyl and when taken together with the attached nitrogen are pyrrolidino, piperidino, morpholino, thiomorpholino or a 4-substituted group of the formula

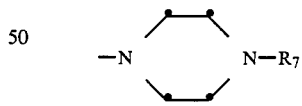

wherein $R_7$ is $C_1$ to $C_4$ alkyl, provided that, when X is hydroxy or protected hydroxy, the compound has the formula 2

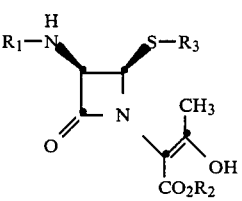    2 wherein $R_1$, $R_2$ and $R_3$ have the same meanings as above.

In the above description of the compounds of this invention, the term "$C_1$–$C_6$ alkyl" refers to the straight and branched chain alkyl hydrocarbon groups such as methyl, ethyl, n-propyl, isopropyl, n-butyl, sec-butyl, n-amyl, isoamyl, n-hexyl, and the like; "$C_1$–$C_3$ cyanoalkyl" refers to such groups as cyanomethyl, 2-cyanoethyl, 3-cyanopropyl, and 2-cyanopropyl; "$C_1$–$C_4$ alkyl" refers to the straight and branched chain alkyl hydrocarbon groups such as methyl, ethyl, n-propyl, isopropyl, n-butyl, t-butyl, and the like; "$C_1$–$C_4$ alkoxy" refers to methoxy, ethoxy, isopropoxy, n-butoxy, and the like; $C_1$ to $C_4$ alkyl sulfide refers to methyl sulfide, ethyl sulfide, isopropyl sulfide, n-butyl sulfide and the like. As used herein, the term "halogen" refers to fluoro, chloro, bromo or iodo. The terms "methylphenyl", "hydroxyphenyl", "protected hydroxyphenyl", "aminophenyl", "protected aminophenyl" and "methoxyphenyl" indicate that the substituent on the phenyl ring can be in the ortho, meta or para position.

When X is a group of the formula

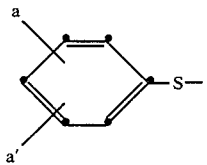

illustrative groups include phenyl sulfide, 4-methylphenyl sulfide, 4-isopropylphenyl sulfide, 4-t-butylphenyl sulfide, 3,4-dimethylphenyl sulfide, 4-ethoxyphenyl sulfide, 3-methoxyphenyl sulfide, 2-methoxyphenyl sulfide; the halo substituted phenyl sulfide groups such as 2-chlorophenyl sulfide, 4-chlorophenyl sulfide, 3,4-dichlorophenyl sulfide, 3-bromophenyl sulfide, 4-fluorophenyl sulfide, 3-fluorophenyl sulfide; the hydroxyphenyl sulfide groups such as 4-hydroxyphenyl sulfide, 3,5-dichloro-4-hydroxyphenyl sulfide, 3-chloro-4-hydroxyphenyl sulfide, 4-methyl-3-chlorophenyl sulfide; the amino substituted phenyl sulfide groups such as 3- or 4-aminophenyl sulfide; the carboxy substituted phenyl sulfide groups such as 4-carboxyphenyl sulfide and 3-carboxyphenyl sulfide, as well as the protected hydroxy, amino and carboxy analogs thereof and like substituted phenyl sulfide groups.

When X is a group of the formula

illustrative groups are those amines that are known and are commercially available such as dimethylamine, diethylamine, di-n-propylamine, di-n-butylamine, dibenzylamine, di-β-phenethylamine, N-methyl benzylamine, N-ethyl butylamine, N-methyl ethylamine, N-methyl isopropylamine, N-ethyl β-phenethylamine, N-(n-propyl)butylamine, and like alicyclic amines, and cyclic amines such as pyrrolidine, piperidine, morpholine, thiomorpholine, 4-methylpiperazine, 4-ethylpiperazine, 4-n-butylpiperazine and the like. Morpholine is the preferred amine.

In the terms "protected amino", "protected hydroxy", and "protected carboxy" and in terms where other moieties are mentioned as bonded to these protected functional groups (e.g. protected hydroxy-phenyl) the term "protected" indicates protecting groups known to those skilled in the cephalosporin art. In particular, these protecting groups must prevent the functional group that they are protecting from reacting with the Grignard reagent used to synthesize the N-ethylidene azetidinone compounds of this invention, and they must be capable of being removed without disrupting the rest of the molecule.

Illustrative hydroxy protecting groups include esters such as the mesitoate and the pivaloate esters, ethers such as the methyl, methoxymethyl, methylthiomethyl, 2-methoxyethoxymethyl, tetrahydro-pyranyl, 4-methoxytetrahydropyranyl, tetrahydrofuranyl, 1-ethoxyethyl, 1-methyl-1-methoxyethyl, t-butyl, allyl, benzyl, triphenylmethyl, t-butyldimethylsilyl, t-butyldiphenylsilyl, tribenzylsilyl, and the triisopropyl-silyl ethers. Preferred hydroxy protecting groups include the tetrahydropyranyl ether, the 4-methoxytetrahydropyranyl ether, the 1-ethoxyethyl ether, the allyl ether, the 1-methyl-1-methoxyethyl ether, the benzyl ether, the t-butyldimethylsilyl ether, and the mesitoate ester.

Illustrative of suitable amino protecting groups include the methyl carbonate group, the N-acetyl, N-chloroacetyl, N-trichloroacetyl, N-trifluoroacetyl, N-4-chlorobutyryl, N-benzoyl and N-phthaloyl amide groups, the N-allyl, N-methoxymethyl, N-benzyloxymethyl, N-tetrahydropyranyl, N-benzyl, N-di(p-methoxyphenyl)methyl, N-triphenylmethyl, and the N-(p-methoxyphenyl)diphenylmethyl alkyl amino protecting groups. The preferred amino protecting groups are the N-acetylamide, N-trichloroacetamide, N-4-chlorobutyryl amide, and the N-phthaloyl amide, and the N-allyl and the N-benzyl alkyl amine groups.

Illustrative carboxy protecting groups are the methyl, benzyl, 4-methoxybenzyl, diphenylmethyl (benzhydryl) and the t-butyl groups.

In the foregoing definitions, hydroxy, amino and carboxy protecting groups are not exhaustively defined. Many such protecting groups are well known in the art and the use of other groups equally applicable to the compounds, such as those described in Theodora W. Greene, "PROTECTIVE GROUPS IN ORGANIC SYNTHESIS", John Wiley & Sons, 1981, New York, will be recognized as suitable. Thus, there is no novelty or inventiveness asserted with regard to the protecting groups in this specification.

Illustrative of the groups in the above definition represented by the following formula where m is O are

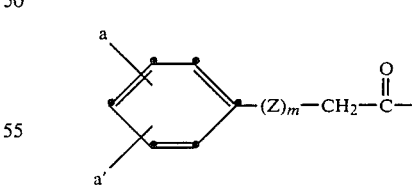

phenylacetyl, 4-methylphenylacetyl, 3-ethylphenylacetyl, 4-isopropylphenylacetyl, 2-methylphenylacetyl, 4-chlorophenylacetyl, 4-bromophenylacetyl, 2,4-dichlorophenylacetyl, 3-bromophenylacetyl, 4-iodophenyl-acetyl, 2-fluorophenylacetyl, 3,4-dihydroxyphenylacetyl, 4-hydroxyphenylacetyl, 3-hydroxyphenylacetyl, 2,6-dimethoxyphenylacetyl, 3-carboxyphenylacetyl, 4-aminophenylacetyl, 3-ethoxyphenylacetyl, 4-methoxyphenylacetyl, 3,4-dimethoxyphenylacetyl, 4-t-butoxyphenylacetyl, 2-carboxyphenylacetyl, 3-chloro-4-methylphenylacetyl and the like. When in the above formula m=1 and Z represents —O—, illustrative groups are the following: phenoxyacetyl, 4-hydroxyphenoxyacetyl, 3-hydroxyphenoxyacetyl, 4-chlorophenoxyacetyl, 3-bromophenoxyacetyl, 3-ethylphenoxyacetyl, 4-methylphenoxyacetyl, 4-hydroxy-3-methylphenoxyacetyl, 4-aminophenoxyacetyl, 2-carboxyphenoxyacetyl, 2-chlorophenoxyacetyl, 4-t-butylphenoxyacetyl, 4-methoxyphenoxyacetyl, 3,4-dimethoxyphenoxyacetyl, 2-aminophenoxyacetyl, 4-isopropoxyphenoxyacetyl and like acyl groups. When in the forgoing formula m=1 and Z represents —S—, illustrative groups are the following: phenylmercaptoacetyl, 4-chlorophenylmercaptoacetyl, 3-hydroxyphenylmercaptoacetyl, 3,4-dimethylphenylmercaptoacetyl, 4-aminophenylmercaptoacetyl, 3,4-dichlorophenylmercaptoacetyl, 3-bromophenylmercaptoacetyl, 4-fluorophenylmercaptoacetyl, 2,6-difluorophenylmercaptoacetyl, 3-fluorophenylmercaptoacetyl, and like groups.

When in formula 1 R' represents a group of the formula

illustrative acyl groups are the mandeloyl group of the formula

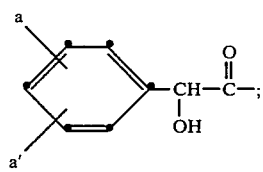

the α-carboxyphenylacetyl group represented by the following formula

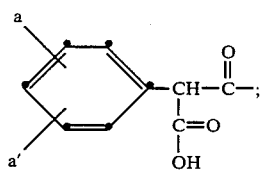

the phenylglycyl group represented by the formula

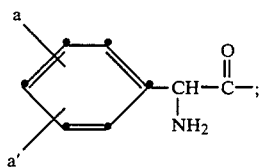

as well as those 2-thienyl and 3-thienyl acyl groups where in the above formula the phenyl group is replaced with a 2-thienyl or 3-thienyl ring. Of course, the hydroxy, carboxy and amino groups can also be in a protected form.

Illustrative of the foregoing acyl groups are 4-methylmandeloyl, 4-hydroxymandeloyl, 3-hydroxymandeloyl, 4-aminomandeloyl, 3-bromomandeloyl, 4-chloromandeloyl, 3-methyl-4-fluoromandeloyl, 2-fluoromandeloyl, 4-fluoromandeloyl, 4-methoxymandeloyl, α-carboxy-4-methylphenylacetyl, α-carboxy-3,4-dichlorophenylacetyl, α-carboxy-4-hydroxyphenylacetyl, α-carboxy-3-hydroxyphenylacetyl, α-carboxy-4-aminophenylacetyl, phenylglycyl, 4-hydroxyphenylglycyl, 3-chlorophenylglycyl, 3-hydroxyphenylglycyl, 4-methoxyphenylglycyl, α-amino-2-thienylacetyl, and α-amino-2-furylacetyl.

When in the above formula 1, R' represents a group of the formula R''—CH$_2$—, examples of such a group are: thien-2-ylacetyl, thien-3-ylacetyl, fur-2-ylacetyl, oxazol-2-ylacetyl, thiazol-2-ylacetyl and tetrazol-1-ylacetyl.

The N-ethylidene azetidinone compounds of the instant invention are made by reacting a substrate cephalosporin of formula 3

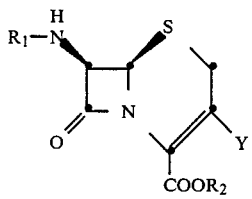

wherein Y is chloro, bromo, C$_1$ to C$_4$ alkoxy, C$_1$ to C$_4$ alkyl sulfide, a group of the formula

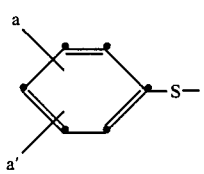

wherein a and a' are as described above for formula 1, or a group of the formula

wherein R$_5$ and R$_6$ are as described above for formula 1, and R$_1$ and R$_2$ is as defined for formula 1, with an alkyl or aryl Grignard reagent in an inert solvent at a temperature between about −80° and 5° C. For this reaction, it is preferred that hydroxy, amino and carboxy groups on the cephalosporin substrate of formula 3 be in the protected form.

Most Grignard reagents will react with compounds of the Formula 3 to provide the corresponding N-ethylidene azetidinones. Certain Grignard reagents are preferred, however. These reagents are represented by the following formula R$_3$MgBr wherein R$_3$ is C$_1$–C$_4$ alkyl or phenyl.

Solvents which can be used in the process are the ether-type solvents such as tetrahydrofuran, dioxane, diglyme, and the like. THF is a preferred solvent.

The Grignard reagents R$_3$MgBr are all known compounds readily prepared by conventional methods. Representative reagents include methylmagnesium bromide, ethylmagnesium bromide, n-propylmagnesium bromide, iso-propylmagnesium bromide, n-butylmagnesium bromide, and phenylmagnesium bromide.

When a 3-chloro or 3-bromo cephalosporin is used as a substrate, the chloro-substituted or the bromo-substituted ethylidene group of the N-ethylidene azetidinone produced reacts with any excess Grignard reagent present to give an alkyl or aryl-substituted ethylidene azetidinone compound of the formula 4

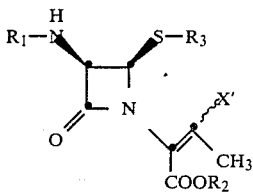

4 wherein X' is the same as $R_3$, and $R_1$ and $R_2$ are the same as defined for formula 1.

The hydroxy-substituted N-ethylidene azetidinone compounds of formula 2

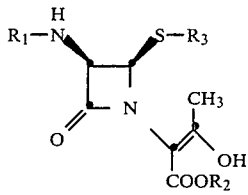

2 are generally made by reacting the solution of a corresponding (4-morpholino)-substituted N-ethylidene azetidinone with acid in the presence of water. Suitable preferred acids include toluenesulfonic acid monohydrate and napthylsulfonic acid monohydrate.

The 3-chloro or the 3-bromo cephalosporin substrates of formula 3 above, (wherein Y is chloro or bromo), are prepared from the corresponding 3-hydroxy compound as described by R. R. Chauvette et al., J. Med. Chem., 18, 403 (1975).

The 3-amino cephalosporin substrates of formula 3 above, (wherein Y is a group of the formula

wherein $R_5$ and $R_6$ are as described for formula 1) are prepared by reacting the corresponding 3-chloro cephalosporin with 2 molar equivalents of the desired amine in a polar organic solvent (i.e., dimethylformamide, tetrahydrofuran, dioxane, etc.) at a temperature between about $-5°$ and $35°$ C. (It should be noted that when Y is a substituted amine, $R_2$ in the above formula 3 cannot be H.) This procedure is described in W. A. Spitzer, U.S. Pat. No. 4,013,651, issued Mar. 22, 1977.

The 3-sulfide cephalosporin substrates of formula 3 (wherein Y is $C_1$ to $C_4$ alkyl sulfide or a group of the formula

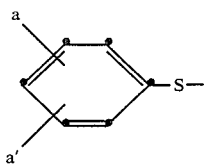

wherein a and a' are as described for formula 1) are prepared by reacting the corresponding 3-chloro cephalosporin with at least an equimolar equivalent amount of thiophenol in an inert organic solvent (i.e. dimethylformamide) in the presence of a suitable base (i.e., sodium hydride) at a temperature between about $-60°$ to about $-25°$ C. These conditions and alternate acceptable procedures are described in R. R. Chauvette et al., U.S. Pat. No. 3,992,377, issued Nov. 16, 1976.

The 3-alkoxy cephalosporins of formula 3 (wherein Y is $C_1$ to $C_4$ alkoxy) are prepared by known procedures. For example, the 3-methoxy compound is prepared by reacting the corresponding 3-hydroxycephalosporin 7-amino nucleus compound in a THF solution with one molar equivalent of triethylamine with excess diazomethane in ether at room temperature. The 3-methoxy nucleus is then acylated with the desired side chain. This procedure is found in R. R. Chauvette et al., J. Med. Chem. 18, 403 (1975).

When $R_2$ is hydrogen and $R_1$ is an acyl group the N-ethylidene compounds of this invention possess antibiotic activity against gram positive and gram negative bacteria. These antibiotic compounds are useful for topical antiseptics.

The following examples further illustrate the compounds of this invention and their methods of preparation.

In the following examples, the abbreviations "NMR", "IR", "MS", "UV", "mmol" and "THF" stand for nuclear magnetic resonance spectrum, infrared spectrum, mass spectrum, ultraviolet spectrum, millimole and tetrahydrofuran, respectively. The n.m.r. spectra were taken on a Varian Associates T-60 instrument, the IR spectra were taken on a Perkin Elmer 281 instrument, the UV spectra were taken on a Cary 118 instrument, and the mass spectrum (electron impact) were obtained on a CEC-21-110A instrument.

EXAMPLE 1

(2R-Cis)-2-(Methyl sulfide)-α-[1-(4-Morpholinyl)ethylidene]-4-Oxo-3-[(Phenoxyacetyl)amino]-1-Azetidineacetic Acid, Methyl Ester A cooled ($-78°$), stirred solution of the methyl 7-(R)-phenoxyacetamido-3-(N-morpholino)-3-cephem-4-carboxylate (1.0 mmol) in 45 ml THF was treated under Ar with 5 equiv. of MeMgBr for 40 minutes ($-78°$), after which 5.0 equivalents of anhydrous HCl were added, or alternatively excess aqueous $NH_4Cl$, followed by warming to $0°$.

The mixture was extracted with ethyl acetate and the extract was washed with water, brine, dried over $Na_2SO_4$, evaporated and chromatographed on Merck silica gel using a toluene-ethyl acetate gradient to give 302 mg (67%) of the title product as a white froth. IR ($CHCl_3$): 1755 cm$^{-1}$; MS m/e: 449, 402, 258, 226, 167, 139; $^1$H NMR δ ($CDCl_3$): 1.97 (s, SMe), 2.02 (s, SMe), 2.19 (s, vinyl Me), 2.52 (s, vinyl Me), 3.2–3.8 (m, morpholinyl), 3.7 (s, CO$_2$Me), 4.6 (s, $\phi$OCH$_2$), 4.92 (d, J=4 Hz, H2), 5.12 (d, J=4 Hz, H2), 5.48 (d,d, J=4 Hz, H3); UV (methanol) $\epsilon_{313}$=20,248.

EXAMPLE 2

(2R-Cis)-2-(Ethyl sulfide)-α-[1-(4-Morpholinyl)ethylidene]-4-Oxo-3-[(Phenoxyacetyl)amino]-1-Azetidineacetic Acid, Methyl Ester and [(2R-Cis), (E)]-α-(1-Hydroxyethylidene)-2-(Ethylsulfide)-4-Oxo-3-[(Phenoxyacetyl)amino]-1-Azetidineacetic Acid, Methyl Ester The experiment of Example 1 was repeated except that EtMgBr was substituted for MeMgBr and the temperature of the subsequent hydrochloric acid hydrolysis rose briefly to 10°. The title product was isolated by chromatography to yield 215 mg (46%) of the morpholinyl ethylidene product: IR (CHCl$_3$): 1755 cm$^{-1}$; MS m/e: 463, 402, 374, 288, 266, 167, 139; $^1$H NMR δ (CDCl$_3$): 1.17 (t, Et), 2.17, 2.42 (both s, vinyl Me), 2.1–2.6 (m, Et), 3.2–3.8 (m, morpholinyl), 3.7 (s, CO$_2$Me), 4.57 (s, $\phi$OCH$_2$), 4.97 (d, J=4 Hz, H2), 5.13 (d, J=4 Hz, H2), 5.47 (d,d, J=4,8 Hz, H3); UV (methanol) $\epsilon_{315}$=22,178; and 104 mg (26%) of the hydroxyethylidene product: IR (CHCl$_3$) 1760 cm$^{-1}$; MS m/e: 394, 365, 333, 318, 288, 237, 204, 176. $^1$H NMR δ (CDCl$_3$) 1.17 (t, Et), 2.17 (s, vinyl Me), 2.47 (q, Et), 3.83 (s, CO$_2$CH$_3$), 4.58 (s, $\phi$OCH$_2$), 5.12 (d, J=5 Hz, H2), 5.54 (d,d, J=5,8 Hz, H3), 12.4 (bs, vinyl OH); UV (methanol) $\epsilon_{267}$=18,094.

EXAMPLE 3

(2R-Cis)-2-(Phenyl sulfide)-α-[1-(4-Morpholinyl)ethylidene]-4-Oxo-3-[(Phenoxyacetyl)amino]-1-Azetidineacetic Acid, Methyl Ester The experiment of Example 1 was repeated, except that C$_6$H$_5$MgBr was substituted for MeMgBr, and upon addition of the C$_6$H$_5$MgBr a gum was formed. The acetone/CO$_2$ bath was then replaced with an ice/H$_2$O bath until the gum dissolved (ca 1 min.). The reaction was then stirred for 30 minutes at −78°. Chromatography yielded 441 mg (86%) of the title product as a white froth. IR (CHCl$_3$): 1755 cm$^{-1}$; MS m/e: 511, 433, 402 226, 167, 139; $^1$H NMR δ (CDCl$_3$): 2.23 (s, vinyl Me), 2.38 (s, vinyl Me), 3.2–3.8 (m, morpholinyl), 3.7 (CO$_2$CH$_3$), 4.57 (s, $\phi$OCH$_2$), 5.3–5.7 (m, H2, H3); UV (methanol) $\epsilon_{317}$=22,243.

EXAMPLE 4

(2R-Cis)-2-(Ethyl sulfide)-α-(1-Methylpropylidene)-4-Oxo-3-[(Phenoxyacetyl)amino]-1-Azetidineacetic Acid, Methyl Ester A cooled (−78°), stirred solution of methyl 7-(R)-phenoxyacetamido-3-chloro-3-cephem-4-carboxylate (625 mg, 1.63 mmol) in THF (50 ml) was treated under an argon atmosphere with EtMgBr (5 equiv.) and the reaction solution was stirred for 15 minutes. Excess hydrochloric acid (1N) was added and the resultant solution was warmed to 0° C. EtOAc was added and the extract washed with H$_2$O, brine, dried and chromatographed on Merck silica using toluene-EtOAc gradient to yield 323 mg (49%) of the title product (62% corrected for starting material). IR (CHCl$_3$): 1760 cm$^{-1}$. MS m/e: 406, 377, 345, 317, 285, 237, 216, 176; $^1$H NMR δ (CDCl$_3$): 1.03–1.30 (m, Ets), 2.2–2.6 (m, Ets), 3.78 (s, CO$_2$CH$_3$), 4.57 (m, $\phi$OCH$_2$), 5.1–5.2 (m, H2), 5.65 (d,d, J=4, 8 Hz, H3).

EXAMPLE 5

(2R-Cis)-2-(Ethyl sulfide)-α-(1-Methoxyethylidene)-4-Oxo-3-[(Phenoxyacetyl)amino]-1-Azetidineacetic Acid, Methyl Ester The experiment of Example 4 was repeated except that methyl 7-(R)-phenoxyacetamido-3-methoxy-3-cephem-4-carboxylate (218 mg, 0.576 mmol) was used as the starting material. The usual isolation procedure yielded two isomers of the title product. These isomers differ at the arrangement of the methyl and methoxy groups bonded to the ethylidene double bond. Isomer A:(45 mg, 19%) IR (CHCl$_3$): 1759 cm$^{-1}$; $^1$H NMR δ (CDCl$_3$): 1.13 (t, Et), 2.2–2.6 (m, Et), 2.53 (s, vinyl Me), 3.73 (s, CO$_2$CH$_3$), 3.83 (s, OMe), 4.57 (s, $\phi$OCH$_2$), 5.13 (d, J=4 Hz, H2), 5.59 (d,d, J=4,9 Hz, H3). Isomer B (26 mg, 11%) IR (CHCl$_3$): 1755 cm$^{-1}$; $^1$H NMR δ (CDCl$_3$): 1.17 (t, Et), 2.23–2.67 (m, Et), 2.25 (s, vinyl Me), 3.75 (s, CO$_2$CH$_3$), 3.90 (s, OMe), 4.60 (s, $\phi$OCH$_2$), 5.24 (d, J=4 Hz, H2), 5.46 (d,d, J=4,8 Hz, H3).

EXAMPLE 6

(2R-Cis)-2-(Ethyl sulfide)-4-Oxo-3-[(Phenoxyacetyl)amino]-α-[1-(Phenylsulfide)ethylidene]-1-Azetidineacetic Acid, Methyl Ester The experiment of Example 2 was repeated except that methyl 7-(R)-phenoxyacetamido-3-phenylsulfide-3-cephem-4-carboxylate (177 mg, 0.388 mmol) was used as the starting material. The usual isolation procedure yielded 117 mg (62%) of the title product. IR (CHCl$_3$): 1765 cm$^{-1}$; MS m/e: 425, 377, 315, 283, 249, 237. MS (FD): 486; $^1$H NMR δ (CDCl$_3$): 1.00–1.33 (m, Et), 2.0–2.6 (m, Et), 2.22 (s, vinyl Me), 3.75 (s, CO$_2$CH$_3$), 6.23 (s, $\phi$OCH$_2$), 5.3–5.8 (m, H2+H3).

EXAMPLE 7

[(2R-Cis), (E)]-α-(1-Hydroxyethylidene)-2-(Methyl sulfide)-4-Oxo-3-[(Phenoxyacetyl)amino]-1-Azetidineacetic Acid, Methyl Ester (2R-Cis)-2-(methyl sulfide)-α-[1-(4-morpholinyl)ethylidene]-4-oxo-3-[(phenoxyacetyl)amino]-1-azetidineacetic acid, methyl ester (219 mg, 0.48 mmol) dissolved in THF (10 ml) was treated with p-toluenesulfonic acid monohydrate (1.25 equiv) at room temperature for 1 hour. EtOAc was added and the extract washed with H$_2$O, NaHCO$_3$, brine, dried and evaporated to yield 126 mg (68%) product. IR (CHCl$_3$): 1760 cm$^{-1}$; MS m/e: 380, 365, 333, 288, 223, 190, 176, 142; $^1$H NMR δ (CDCl$_3$): 2.00 (s, SMe), 2.16 (s, vinyl Me), 3.83 (s, CO$_2$CH$_3$), 4.58 (s, $\phi$OCH$_2$), 5.07 (d, J=4 Hz, H2), 5.53 (d, d, J=4,10 Hz, H3), 12.3 (bs, vinyl OH); UV (methanol) $\epsilon_{267}$=19,021.

EXAMPLE 8

[(2R-Cis), (E)]-α-(1-Hydroxyethylidene)-2-(Phenyl sulfide)-4-Oxo-3-[(Phenoxyacetyl)amino]-1-Azetidineacetic Acid, Methyl Ester The experiment of Example 7 was repeated, except that (2R,-cis)-2-(phenyl sulfide)-α-[1-(4-morpholinyl)ethylidene]-4-oxo-3-[(phenoxyacetyl)amino]-1-azetidineacetic acid, methyl ester (419 mg, 0.819 mmol) was used as the starting material. The usual isolation procedure yielded 331 mg of the title product. IR (CHCl$_3$): 1763 cm$^{-1}$; MS m/e: 397, 370, 332, 302, 288, 256, 222; $^1$H NMR δ (CDCl$_3$): 2.23 (s, vinyl Me), 3.67 (s, CO$_2$CH$_3$), 4.53 (s, φOCH$_2$), 5.33–5.67 (m, H2+H3), 12.2 (bs, vinyl OH); UV (methanol) ε$_{254}$=21,690 (broad peak).

EXAMPLE 9

(2R-Cis)-2-(Ethyl sulfide)-α-[1-(4-Morpholinyl)ethylidene]-4-Oxo-3-[(2-Thiopheneacetyl)amino]-1-Azetidineacetic Acid, Benzhydryl Ester A cooled (−78°), stirred solution of benzhydryl 7-(R)-[2-(thien-2-yl)acetamido]-3-(4-morpholino)-3-cephem-4-carboxylate (1.0 mm) in 25 ml THF was treated under argon with 5.0 equiv. EtMgBr for 30 minutes. Excess aqueous NH$_4$Cl was added and the reaction mixture warmed to 0°. EtOAc was added and the extract washed with H$_2$O, brine, dried over Na$_2$SO$_4$, evaporated and chromatographed on silica gel using a toluene-EtOAc gradient to give 454 mg (65.5%) of the title product as a froth. IR (CHCl$_3$): 1755 cm$^{-1}$; MS m/e: 605, 394, 334, 276, 247, 227, 199, 167; $^1$H NMR δ (CDCl$_3$): 0.80–1.18 (m, Et), 2.07 (s, vinyl Me), 2.0–2.4 (m, Et), 3.23–3.73 (m, morpholinyl), 3.78 (s, thiophene methylene), 4.80–4.97 (m, H2), 5.27 (d,d, J=4,8 Hz, H3).

EXAMPLE 10

[(2R-Cis), (E)-α-(1-Hydroxyethylidene)-2-(Ethyl sulfide)-4-Oxo-3-[(2-Thiopheneacetyl)amino]-1-Azetidineacetic Acid, Benzyhydryl Ester (2R-cis)-2-(ethylthio)-α-[1-(4-morpholinyl)-ethylidene]-4-oxo-3-[(2-(thien-2-yl)acetyl))amino]-1-azetidineacetic acid, benzhydryl ester (454 mg, 0.749 mm) in 25 ml THF was treated with 1.25 equiv. p-toluene-sulfonic acid monohydrate and allowed to react at room temperature for 1 hr. EtOAc was added and the extract washed with H$_2$O, NaHCO$_3$, brine, dried (Na$_2$SO$_4$) and evaporated to give 0.364 g (90.5%) product as a yellow froth. IR (CHCl$_3$): 1765 cm$^{-1}$; MS m/e 463, 430, 387, 326, 312, 297, 265, 247, 227, 206, 184, 167, 146, 97; $^1$H NMR δ (CDCl$_3$): 1.0 (t, J=7 Hz, Et), 2.07 (s, vinyl Me), 2.13–2.40 (m, Et), 3.77 (s, thiophene methylene), 5.0 (d, J=4 Hz, H2), 5.37 (d,d, J=4,8 Hz, H3).

I claim:

1. A compound of the formula

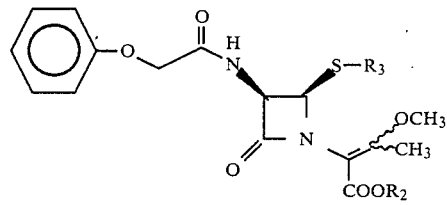

wherein:

R$_2$ is hydrogen, methyl, benzyl, 4-methoxybenzyl, diphenylmethyl, or t-butyl; and R$_3$ is C$_1$ to C$_4$ alkyl or phenyl.

2. A compound of claim 1, wherein R$_3$ is ethyl.

3. A compound of claim 2, wherein R$_2$ is hydrogen or methyl.

4. A compound of the formula

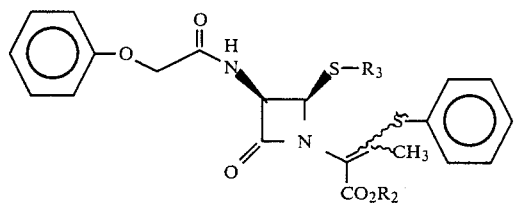

wherein:

R$_2$ is hydrogen, methyl, benzyl, 4-methoxybenzyl, diphenylmethyl, or t-butyl; and R$_3$ is C$_1$ to C$_4$ alkyl or phenyl.

5. A compound of claim 4, wherein R$_3$ is ethyl.

6. A compound of claim 5, wherein R$_2$ is hydrogen or methyl.

* * * * *